United States Patent [19]
Forsyth et al.

[11] B 3,991,209
[45] Nov. 9, 1976

[54] HALOMETHANESULFONAMIDES FOR ERADICATING INTERNAL PARASITES

[75] Inventors: Bruce Adam Forsyth, Croydon; Richard Burridge Warner, Ringwood, both of Australia

[73] Assignee: ICI Australia Limited, Melbourne, Australia

[22] Filed: Oct. 21, 1974

[21] Appl. No.: 516,804

[44] Published under the second Trial Voluntary Protest Program on March 23, 1976 as document No. B 516,804.

[30] Foreign Application Priority Data
Nov. 13, 1973 Australia............................ 5637/73
Nov. 27, 1973 Australia............................ 5787/73

[52] U.S. Cl. ............................................. 424/321
[51] Int. Cl.² ........................................... A01N 9/16
[58] Field of Search ................................. 424/321

[56] References Cited
UNITED STATES PATENTS

| | | | |
|---|---|---|---|
| 3,607,935 | 9/1971 | Hilmer et al. | 424/321 |
| 3,609,187 | 9/1971 | Moore et al. | 424/321 |
| 3,622,625 | 11/1971 | Wolf et al. | 424/321 |
| 3,795,743 | 3/1974 | Okuda et al. | 424/321 |

*Primary Examiner*—Frederick E. Waddell
*Attorney, Agent, or Firm*—Cushman, Darby & Cushman

[57] ABSTRACT

A method of treating warm blooded animals to eradicate certain internal parasites; which method comprises administering to said warm blooded animals a therapeutic dose of a composition comprising as active ingredient a compound of formula I.

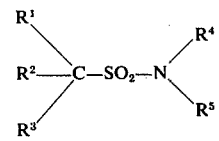

wherein $R^1$, $R^2$ and $R^3$ which may be the same or different are hydrogen, or halogen and at least two of $R^1$, $R^2$, and $R^3$ are halogen, and $R^4$ and $R^5$ which may be the same or different are selected from the group consisting of hydrogen, alkyl containing from 1 to 6 carbon atoms, —$NHR^6$ where $R^6$ is hydrogen or an alkyl group containing from 1 to 6 carbon atoms; and when either $R^4$ or $R^5$ is —$NHR^6$ then $R^5$ or $R^4$ respectively is hydrogen.

7 Claims, No Drawings

HALOMETHANESULFONAMIDES FOR ERADICATING INTERNAL PARASITES

This invention relates to compositions for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in mild yield from liver fluke infection will also occur and in addition the loss sustained by the condemnation of infected livers as human food may also be considerable.

An example of nematode is *Haemonchus contortus* which is a nematode parasitic in the abomasum of fourth stomach of ruminants. It is a blood sucking parasite and when present in large numbers can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a class of compounds which are effective in killing liver fluke.

Accordingly we provide a method of treating warm blooded animals to eradicate certain internal parasites; which method comprises administering to said warm blooded animals a therapeutic dose of a composition comprising as active ingredient a compound of formula I

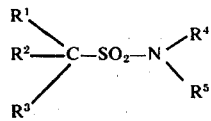

wherein $R^1$, $R^2$ and $R^3$ which may be the same or different are hydrogen, or halogen and at least two of $R^1$, $R^2$, and $R^3$ are halogen and $R^4$ and $R^5$ which may be the same or different are selected from the group consisting of hydrogen, alkyl containing from 1 to 6 carbon atoms, —$NHR^6$ where $R^6$ is hydrogen or an alkyl group containing from 1 to 6 carbon atoms; and when either $R^4$ or $R^5$ is —$NHR^6$ then $R^5$ or $R^4$ respectively is hydrogen. Preferably $R^1$ and $R^2$ are the same and are fluorine, bromine or chlorine and $R^3$, $R^4$ and $R^5$ are hydrogen.

The process of the present invention has utility in the field of animal therapy. It is effective against both mature and immature liver fluke of the *Fasciola* genus especially *Fasciola hepatica* and *Fasciola gigantica*. Many of the compositions also possess activity against nematodes such as *Haemonchus contortus*.

For effective treatment, certain dosage levels are desired depending upon the compound employed, the type of animal to be treated, and the particular helminth being combatted. In general, effective fluke efficacy is achieved when the composition is administered in a single dose at dosage levels of from about 25 to 200 mg active ingredient/kg of animal body weight, and preferably from about 50 to 100 mg active ingredient per kg of animal body weight.

The compositions of the present invention may be administered in a variety of ways, depending upon the particular animal employed, the type of anthelmintic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials.

The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as a feed premix to be later admixed with the animal's food.

When the compositions are to be solid unit dosage forms as in tablets, capsules, or boluses, the ingredients other than the active ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitable admixed with an acceptable base vehicle. In all of such forms, i.e. in tablets, bolues, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antifoam compounds, and the like may be employed. Such a dry product may contain as much as 95% by weight of the active compound, the rest being contributed by the excipients. Preferably, the solid composition contains from 30% to 95% by weight of the active compound. Enough water should be added to the solid product to provide the proper dosage level within a convenient amount of liquid for a single oral dose. Liquid formulations containing up to 70 weight percent of dry ingredients will in general be suitable with the preferred range being from 5 to 50 weight percent.

Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soyal flour, soybean mill feed, antibiotic mycelia, soyal grits, crushed limestone and the like are all suitable. The active compounds are intimately dispersed or amixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05 – 25% in the feed. As stated above, animals are preferably treated at a time when the infestation is apparent or suspected and the most preferred method for such treatment is via the single dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or propylactic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals.

Preferably the compositions are administered to the animal by parenteral dose and in a further aspect of our invention we provide an injectable composition comprising a sterile aqueous solution containing from 5 to 70% w/w preferably 5 to 50% w/w of the active ingredient.

The composition may be sterilized by methods known to those skilled in the art for the sterilization of injectable solution such as, for example, ultra filtration or gamma radiation.

The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachloroethylene, organic and inorganic arsenical compounds, tetramisole, 2-phenyl-benzimidazole, thiabendazole, phenothiazine, mebendazole and pyrantel salts.

A particularly preferred composition according to our invention comprises an aqueous composition containing from 5 to 50% w/w of the active ingredient of formula I and from 0.1 to 25% w/w of L-tetramisole free base in the form of its acid salt, preferably the hydrochloride or phosphate salt. This composition is of use as a drench or, if sterilized, as an injectable solution for treatment of warm blooded animals infected with a wide variety of helminths.

The invention is now illustrated by, but by no means limited to, the following examples in which all parts are part by weight unless otherwise specified.

EXAMPLE 1

An aqueous solution of each test compound was sterilized by filtration through a bacteriological filter and used as either a subcutaneous injection or an oral drench to dose sheep known to be infected with adult *Fasciola hepatica*.

Sheep which were known to be infected with adult *Fasciola hepatica* were dosed as shown in Table I with solutions of the various test compounds.

The effect on Fasciola was measured initially by the change in the rate at which eggs appeared in the faeces. Samples of faeces were drawn just before dosing and at weekly intervals for a period of up to 3 weeks after dosing. The samples were homogenised and diluted with water and the number of eggs per gram were assessed by standard procedures. The results are shown in Table I.

TABLE I

| Dose rate mg/kg body weight and mode of administration | | Test compound | Faecal egg count on days shown | | | |
|---|---|---|---|---|---|---|
| | | | 0 | 7 | 14 | 21 |
| 70 | oral | $Cl_3C\ SO_2\ NH_2$ | 315 | 145 | 25 | 0 |
| 50 | " | " | 800 | 35 | 15 | 0 |
| 70 | " | $Cl_2CH\ SO_2\ NH_2$ | 800 | 0 | 5 | 30 |
| 50 | " | $F_3C\ SO_2\ NH_2$ | 3050 | 0 | 75 | 15 |
| 50 | " | $F\ CH_2\ SO_2\ NH_2$ | 265 | 245 | 0 | 0 |
| | | $F,\ Cl\ CH\ SO_2\ NH_2$ | | | | |

We claim:

1. A method of treating a warm blooded animal to eradicate internal parasites selected from the group consisting of trematodes and nematodes; which method comprises orally or parenterally administering to said warm blooded animal an effective amount of a composition comprising as active ingredient a compound of the formula

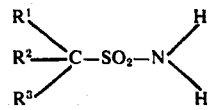

wherein $R^1$, $R^2$ and $R^3$ which may be the same or different are hydrogen, or halogen and at least two of $R^1$, $R^2$, and $R^3$ are halogen.

2. A method according to claim 1 wherein $R^1$ and $R^2$ are the same and are fluorine, bromine or chlorine and $R^3$ is hydrogen.

3. A method according to claim 1 wherein the parasite eradicated is Fasciola sp.

4. A method according to claim 1 wherein the parasite eradicated is Haemonchus contortus.

5. A method according to claim 1 wherein the composition is administered in a single dose at dosage levels of from about 25 to 200 mg active ingredient/kg of animal body weight.

6. A method according to claim 5 wherein the single dose is at dosage levels of from 50 to 100 mg active ingredient per kg of animal body weight.

7. A method according to claim 1 wherein $R^1$ is hydrogen, $R^2$ is chlorine and $R^3$ is fluorine.

* * * * *